United States Patent [19]

Hsiung

[11] 3,931,912
[45] Jan. 13, 1976

[54] TWO-PART HAIR DYE OR HAIR BLEACH PACKAGE

[75] Inventor: Du Yung Hsiung, Park Forest, Ill.

[73] Assignee: The Gillette Company, Boston, Mass.

[22] Filed: Oct. 7, 1974

[21] Appl. No.: 512,844

Related U.S. Application Data

[63] Continuation of Ser. No. 171,398, Aug. 12, 1971, abandoned, which is a continuation-in-part of Ser. No. 846,580, July 31, 1969, abandoned.

[52] U.S. Cl. .......................... 222/94; 8/10.2; 8/11; 8/32; 8/79; 8/111; 206/216; 206/219; 222/136; 222/192; 424/DIG. 1; 424/DIG. 2; 424/47; 424/62
[51] Int. Cl.² ........................................ B65D 35/22
[58] Field of Search ............ 8/10.2, 11, 32, 79, 111; 424/47, 62, DIG. 1, DIG. 3; 222/94, 4, 82, 136; 206/216, 219

[56] References Cited
UNITED STATES PATENTS

| | | | |
|---|---|---|---|
| 2,283,350 | 5/1942 | Baum | 424/62 |
| 3,128,232 | 4/1964 | Wilmsmann et al. | 8/10.2 |
| 3,193,464 | 7/1965 | Edman et al. | 424/62 |
| 3,210,252 | 10/1965 | Blanke et al. | 8/10.2 |
| 3,326,416 | 6/1967 | Hayes | 222/2 |
| 3,337,411 | 8/1967 | Wilmsmann et al. | 8/10.2 |
| 3,339,802 | 9/1967 | Weiner et al. | 222/82 |
| 3,341,418 | 9/1967 | Moses | 424/47 X |
| 3,415,608 | 12/1968 | Tucker | 8/10.2 |

FOREIGN PATENTS OR APPLICATIONS

| | | | |
|---|---|---|---|
| 831,851 | 4/1960 | United Kingdom | 8/10.2 |
| 1,125,528 | 8/1968 | United Kingdom | 8/10.2 |

Primary Examiner—Albert T. Meyers
Assistant Examiner—Vera C. Clarke

[57] ABSTRACT

A pressurized package containing a conventional pressure propellant is divided into two compartments arranged for mixing of their contents simultaneously with dispensing, one compartment containing a peroxide solution and the other containing a hair treating composition including certain selected compounds in quantity sufficient to prevent development of unsafe pressure should the peroxide decompose within the package.

17 Claims, No Drawings

TWO-PART HAIR DYE OR HAIR BLEACH PACKAGE

This is a continuation of application Ser. No. 171,398, filed Aug. 12, 1971, now abandoned, which in turn is a continuation-in-part of application Ser. No. 846,580, filed July 31, 1969, now abandoned.

This invention relates to pressure packaged liquid compositions, pertaining more specifically to two-part compositions, one part of which includes hydrogen peroxide, in which the two parts are adapted to be mixed only during discharging or dispensing from the container in which they are packaged. The invention is particularly concerned with such pressurized dispensing packages containing two-part hair treating compositions, such as oxidative dyes and bleaches.

Treatment of human hair with direct dyes, a procedure generally known as tinting, results in a final color which is a combination of the natural color of the hair (which is left unchanged) and the added color imparted by the dye. In some other processes, the natural pigments in the hair are first removed by treatment with an oxidizing agent such as alkaline hydrogen peroxide after which the desired color is imparted to the fibers by treatment with oxidative dyestuffs such as p-phenylenediamine or p-tolylenediamine which are converted in the hair fiber to high molecular weight colored compounds by the action of atmospheric oxygen or by chemical oxidizing agents such as hydrogen peroxide. It is also possible to practice this method by concurrently conducting the bleaching and dyeing steps, i.e., the alkaline hydrogen peroxide bleaches the hair while the dyestuff is simultaneously penetrating the hair fibers and being oxidized to produce the desired color.

In the usual procedure of carrying out the dyeing or combined bleaching and dyeing operation, the oxidative dye base is thoroughly mixed in a container with hydrogen peroxide and applied to the hair in such a manner as to ensure complete saturation of the hair including the root portions. This method is, of course, time-consuming and subject to mixing errors leading to the development of insufficient color or hair damage through the use of excess peroxide. There is an additional possibility that for one reason or another the composition cannot be applied to the hair immediately after mixing but only after a period of time has elapsed. Since the oxidative dye precursors begin to oxidize immediately upon exposure at atmospheric oxygen or hydrogen peroxide, it is evident that an undesirable color effect may result if a partially oxidized composition is used.

There have been various proposals in the past for the packaging of oxidative hair dyeing compositions in pressurized dispensing devices for the purpose of obviating some of the disadvantages enumerated above. It has been proposed to provide a pressurized package with two interior compartments, the contents of which are kept separate from one another until it is desired to use the compositions. However, because of the necessity for making patch tests of the mixed composition on the skin many hours, usually a day, before actual use of the composition, it has been impossible to employ packages which provide for mixing of the entire contents of the two compartments prior to dispensing from the container, as in the case of British Pat. No. 1,125,528 and U.S. Pat. No. 3,318,484. As pointed out above, the mixed composition remains useful for its intended purpose for only a short time after mixing.

While there have been other proposals to package hair dyes in two-part containers which provide for mixing of the parts simultaneously with dispensing, as in the case of U.S. Pat. Nos. 3,272,389 and 3,341,418, the risk of accidental or premature mixing of the contents of the two compartments by leakage or by rupture of one of the compartments or by permeation through the wall separating the compartments has been considered to present a serious hazard. Not only is the mixture useless within a short time, but in addition, the generation of gaseous oxygen by decomposition of the peroxide upon contact with the ingredients of a conventional oxidative dye base composition, particularly when the mixture is alkaline, which has been known to occur, leads to excessively high pressures in the container and the danger of explosion unless special precautions are taken in the construction of the container.

It has now been found that the generation of excessively high pressures in a two-compartment container brought about by the decomposition of a hydrogen peroxide composition contained in one compartment can be prevented by the incorporation in the other compartment of a composition containing one or a mixture of certain chemical control compounds. Some of these control compounds are primary oxidative dye intermediates (color formers) of the type long used in the conventional practice of oxidative hair dyeing. Other of these compounds are couplers or color modifiers also long used in the practice of oxidative hair dyeing to modify the color produced by the primary oxidative dye intermediates. Yet other of these compounds are materials not heretofore known to be useful in the practice of oxidative hair dyeing. It has been found that by adjusting the relative proportions of the selected control compound or mixture of such compounds with respect to the peroxide and with respect to the volume of free space within the container, the generation of gaseous oxygen from the peroxide can be reduced to safe limits or completely eliminated, making it possible to employ a container of conventional lightweight construction of the type employed for packaging other compositions with the usual pressure propellants. While any suitable two-compartment pressurized container which provides for mixing simultaneously with dispensing may be used in the package of the present invention, the container used in the preferred embodiment is that shown in U.S. Pat. No. 3,241,722. The thin flexible wall of the inner container in the dispensing device of U.S. Pat. No. 3,241,722 which separates the contents of the inner container from those of the outer container is conventionally made of polyethylene, polypropylene, cellulose acetate or other synthetic plastic material and is subject to permeation to a greater or lesser extent by the contents of the two containers in some cases as well as being subject to rupture. The invention provides protection against leakage or diffusion of the peroxide through the separating wall followed by a reaction liberating oxygen within the second container.

In the case of conventional pressure containers in which the pressure is provided by the usual propellants such as liquefied gaseous propellants, it is essential to provide some free space (i.e., space filled with gas or vapor, not with liquid or solid) within the filled container in order to avoid risk or rupture of the container when exposed to high temperatures during shipment and storage prior to use. The minimum such free space is about 5% while the maximum is dictated by governmental regulation and the undesirably higher costs of providing a given quantity of product in an "oversized" container. It is usually desirable to limit free space to a maximum of 50%. Desirably, the fill level for products of this type provides a free space of from about 10 to about 40%; preferably, from about 20 to about 40%.

The present invention makes it possible to fill containers to the same extent, i.e., to have a minimum of approximately 5% free space or volume within the container (including both compartments) without appreciable increase in risk of rupture of the container if premature mixing of the contents of the two compartments occurs.

In general, pressures within the container up to 150 p.s.i.g. at 25°C. can be tolerated without excessive risk of rupture. In practical terms, this means, when the free space is as little as 5% of the total volume, enough of the selected compound or compounds must be used to prevent substantially completely the liberation of gaseous oxygen should the two parts become inadvertently mixed. Depending on which compound or compounds are used, this amounts to about 50% to about 500% by weight of the peroxide (calculated as hydrogen peroxide). When the free space is higher, of course, the liberation of some oxygen can be tolerated provided the total pressure within the container does not exceed 150 p.s.i.g. Accordingly, the minimum amount of total compound needed for safety can be less when the free space is high than when the free space is the minimum 5% by volume.

In the case where the free space amounts to 50% of the total, the total amount of compound needed for safety can be as low as about 10% by weight of the peroxide (calculated as hydrogen peroxide). When the amount of free space is at some value between 5% and 50%, the minimum amount of total control compound required varies approximately proportionately. In the case where the free space amounts to 10 to 25% of the total, at least 25% of the control compound by weight of the peroxide must be used.

The quantity and species of compounds to be used in any given situation is dependent upon three factors: the amount of peroxide present and capable of decomposing to form oxygen, the amount of free space, and the final color result desired.

Primary oxidative dye intermediates (color formers) which have been found to be effective in controlling or limiting generation of oxygen from peroxide solutions when used as described above include o-aminophenol, p-aminophenol, methyl-p-aminophenol, 4-amino-3-methylphenol, 2,4-diaminophenol, N-(p-hydroxyphenyl) glycine, p-phenylenediamine, p-tolylenediamine and 1,2,4,5,-tetrahydroxybenzene.

In the formulation of oxidation dyes, it is usual for all shades of color to employ an excess of primary intermediates over the amount of couplers or modifiers in order to ensure that no free coupler or modifier remains on the hair, a result which is undesirable because some of them are extremely substantive to hair and any excess tends to remain in the hair until, on subsequent dyeing, it tends to produce off-shade results. In the formulation of dark brown or black shades, even larger excess quantities of primary intermediates are customarily used to ensure depth of color. In these shades, it is also less necessary that the originally present hair pigment (if any) be bleached in order to provide the desired color, thus relatively smaller quantities of peroxide are required. In many such formulations, the quantity of primary intermediates and of modifiers or couplers required for the desired color development may also be sufficient to reduce or eliminate the generation of oxygen should the peroxide and dye base compositions become inadvertently mixed.

In the formulation of lighter shades, however, i.e., those containing relatively smaller quantities of primary intermediates and requiring substantial bleaching of the hair if originally dark, it is usually necessary to add control compounds beyond the quantity required solely for color development in order to practice the invention.

We have found that, if a composition is formulated to give the desired color effect on hair, but does not comprise sufficient total primary intermediates to provide adequate pressure control, careful selection of control compounds which are not primary intermediate compounds can provide for adequate pressure control without adversely affecting the color produced on dyeing or on subsequent re-dyeing. In such compositions, the amount of total primary intermediate of the total compound is normally less than that of the total remainder of the control compounds.

The choice of the control compound added can have an important effect upon the final color result. It is expedient first to formulate for the desired shade or color alone without regard to total quantity of primary intermediates, modifiers or couplers used, and then to introduce an additional quantity of another control compound which does not appreciably change the final color or shade. The preferred such control compounds having little or no effect upon color are beta-naphthol and 2,5-dihydroxybenzoic acid, both of which have been found to be particularly useful in the formulation of compositions ranging from a hair lightener or bleach producing no color, in which neither primary intermediates nor modifiers nor couplers are normally used and in which the compounds provide only pressure control, to compositions producing light brown shades, some of which do not employ sufficient quantities of primary intermediates and modifiers or couplers to ensure sufficient pressure control. Other control compounds effective to control generation of oxygen produce only very light colors upon mixing with peroxide solution and hence are particularly useful in formulating light brown shades, although they are not as desirable as the two first named for use in hair lighteners or bleaches; these include: 3,4-dihydroxybenzoic acid, gallic acid, propyl gallate, 2,7-naphthalenediol, 2,2',4-,4'-tetrahydroxybiphenyl, hydroquinone monosulfonic acid, 3,4,5-trihydroxyacetophenone and 3-(N,N-dimethylamino) phenol.

Other control compounds produce somewhat more intense colors and are therefore more limited in utility; these include: 8-hydroxyquinoline, pyrocatechol, resorcinol, hydroquinone, pyrogallol, 1,3,5-trihydroxybenzene, 4-t-butyl catechol, 1,5-naphthalenediol, 3-hydroxydiphenylamine, m-phenylenediamine, and 2,4-diaminoanisole. While these are not normally considered primary intermediates in hair dyes, they can be used along with primary intermediates to produce dark colors and to provide control of pressure.

The nature of the reaction by which the expected development of oxygen pressure from the peroxide is altered or suppressed is not fully understood, since the molar ratio of the minimum amount of total control compound or mixture of compounds to the amount of peroxide is frequently as low as about 0.10.

In the pressure package of the present invention, the peroxide, stabilizers for the peroxide, and a portion of the total water are preferably placed in one compartment, while all of the remaining ingredients of the oxidative dye composition are placed in the other compartment. When alkalizing agents are present, they are preferably placed in the second compartment separate from the peroxide. The pressure propellant can be placed in either compartment or in both. In the preferred container of U.S. Pat. No. 3,241,722, the peroxide-containing component is preferably placed in the inner compartment, while the propellant along with the remaining ingredients of the composition is placed in the outer compartment, the wall separating the two compartments preferably being composed of synthetic plastic material such as polyethylene, polypropylene, cellulose acetate, etc. which is more readily ruptured than the outer wall of the container which is preferably metallic.

Except for the requirement that sufficient of the control compound or mixture of compounds be used to ensure against excessive pressure build-up in the event of inadvertent mixing of the peroxide component and the other component, conventional hair dye and aerosol product formulation techniques may be employed in the practice of this invention.

In the preferred form of the invention, the control compounds are formulated into an aqueous composition to which are added any necessary ingredients to provide the desired final pH, and to supply the composition with the requisite shelf stability and application characteristics. In order to provide an aesthetically acceptable foam upon expulsion from the pressurized package and to improve penetration of the dye composition into the hair, small amounts of soaps and certain wetting agents are preferably incorporated. While any of the alkalizing agents known to be useful in the formulation of oxidative hair dyeing compositions, including fixed alkalis such as sodium or potassium hydroxide, ammonia, or various amines, may be employed in the practice of this invention, it is preferred to use short chain alkanolamines, such as monoethanolamine, as described and claimed in my copending application Ser. No. 826,661, filed May 12, 1969, now abandoned.

The compositions of this invention, like conventional oxidative hair dyeing compositions, work broadly at a pH of 7.0 to 12.0. Where it is desired to bleach the hair as well as impart a new color to the fibers, it is preferred that the amount of alkaline material be sufficient to provide in the mixed composition a final pH of 9 to 11. Where bleaching is not required, i.e., where the final hair color is not to be lighter than the natural color, a pH as low as 7.0 will be found to be useful.

When it is desired merely to enhance or add to the natural color of the hair, it has been found expedient to limit the peroxide concentration to 0.1% to 2.0% by weight of the total contents of the package, excluding propellants, with 1.5% being preferred. Within this range, there is sufficient peroxide to develop the final color of the dye intermediates used but insufficient peroxide to have any substantial bleaching effect on the natural pigments of the hair. When it is desirable to lighten or bleach the natural color of the hair while developing the new color within the fiber, a range of 2% by weight and more up to 6% is useful, the preferred range being 3.0 to 4.5% by weight, based on total contents exclusive of propellants. Within this range substantial bleaching of the natural pigments occurs so that the final color result may be substantially lighter than the natural color of the hair.

The pH of the peroxide component whether or not mixed with propellant can be from 2.5 to 7.5, but is preferably within the range of 3.5 to 4.5.

It is desirable that the total contents of the package, exclusive of propellant, amount to approximately 100-120 grams in order to suffice for saturating a single large head of hair; larger quantities, for treating multiple heads of hair may be present in a single package if desired.

Any conventional liquified gaseous propellant may be employed in conjunction with the compositions of the present invention. Among the most useful and readily available are hydrocarbons such as n-butane or isobutane present alone or in mixtures thereof with propane; and halogenated hydrocarbons such as those sold under the trademark Freon, for example, dichlorodifluoromethane, monochlorotrifluoromethane, trichlorotrifluoroethane, dichlorotetrafluoroethane, etc. Compressed gas propellants such as nitrogen may also be used either alone or in conjunction with the foregoing liquified gaseous propellants.

The composition is applied directly to the hair as it is dispensed from the package, the two-part composition being mixed during the dispensing operation and virtually simultaneously with its application to the hair. The composition is allowed to remain on the hair for sufficient time to develop the desired shade of color, after which the hair is rinsed and shampooed in the usual manner. While the composition may be left in contact with the hair for time periods from 2 minutes to 90 minutes, a period from 10 to 20 minutes is usually most satisfactory and convenient.

The following specific examples are intended to illustrate more fully the nature of the invention but are not intended to be a limitation upon its scope.

EXAMPLE 1

To measure the pressure of gaseous oxygen generated inside a container by mixing a conventional dye base component (lacking any dye intermediate or modifier) with a conventional stabilized peroxide component in the absence of pressure propellant, the following compositions were prepared:

| Part I | % by weight |
|---|---|
| Oleic acid | 8.7 |
| Monoethanolamine | 6.7 |
| Isopropanol | 1.9 |
| Octyl phenoxy polyethoxy ethanol | 1.9 |
| Lauryl alcohol | 0.4 |
| Water | to 100 |

| Part II | | % by weight |
|---|---|---|
| Hydrogen peroxide | | 16.0 |
| Phenacetin | Stabilizers | 0.04 |
| Sodium stannate | | 0.0045 |
| Deionized water | | to 100 |
| Phosphoric acid | | to pH 4.0 |

Ninety gm. of Part I and 30 gm. of Part II were mixed together in a lined aluminum pressure can leaving 47% free space, i.e., filling 53 percent of the total volume of the can. The can was immediately crimped with a standard aerosol valve and cup. The pressure inside the can was continuously measured for 24 hours comparison with a mixture identical except for the incorporation of 2% beta-naphthol in Part I showed the following results:

| | Pressure (psig) | |
|---|---|---|
| Time | Control Mixture | Control Mixture +beta-naphthol |
| 0 | 0 | 0 |
| 4 hours | 25 | 0 |
| 6 hours | 74 | 0 |
| 7 hours | 100 | 0 |
| 24 hours | 160 | 0 |

The results show that the addition of 2% beta-naphthol completely prevented the build up of oxygen pressure.

EXAMPLE II

Various control compounds, including some dye intermediates and modifiers, alone and in combination, were evaluated as described in Example I by including 1-2% of each in Part I of a test mixture except that the pressure was measured after 3 days instead of measuring pressures after shorter time intervals. The following results were obtained:

| Control Compound | % by Weight | Pressure (psig) |
|---|---|---|
| None | — | 180 |
| Resorcinol | 2.0 | 1 |
| m-Phenylenediamine | 2.0 | 8 |
| p-Phenylenediamine | 2.0 | 18 |
| Pyrogallol | 2.0 | 16 |
| 2,7-napthalenediol | 2.0 | 0 |
| Hydroquinone | 2.0 | 6 |
| m-Phenylenediamine | 1.0 | |
| Resorcinol | 1.0 | 0 |
| m-Phenylenediamine | 1.0 | |
| Pyrogallol | 1.0 | 0 |
| m-Phenylenediamine | 1.0 | |
| 2,7-napthalenediol | 1.0 | 3 |
| p-Phenylenediamine | 1.15 | |
| Resorcinol | 0.20 | 29 |
| 2,4-Diaminoanisole | 0.33 | |
| Catechol | 1.0 | 8 |
| 2,4-Diaminoanisole | 2.0 | 0 |
| 3,4-Dihydroxybenzoic acid | 1.0 | 10 |
| Hydroquinone sulfonic acid, potassium salt | 1.0 | 43 |
| 3-(N,N-Dimethylamino)phenol | 2.0 | 7 |
| 4-t-Butyl catechol | 1.0 | 11 |
| 2,5-Dihydroxybenzoic acid | 1.0 | 2 |

Analysis of the above mixtures for residual hydrogen peroxide after 3 days showed substantial decomposition of the peroxide in all cases.

EXAMPLE III

The following compositions were prepared:

| Part I | % by weight |
|---|---|
| Oleic acid | 8.7 |
| Octyl phenoxy polyethoxy ethanol | 6.0 |
| Isopropanol | 10.0 |
| Monoethanolamine | 5.0 |
| Methyl-p-aminophenol | 0.1 |
| 4-Nitro-1,2-diaminobenzene | 0.003 |
| Beta-napthol | 1.0 |
| Water | to 100 |

| Part II | % by Weight |
|---|---|

-continued

| Part I | % by weight |
|---|---|
| Hydrogen peroxide | 16.0 |
| Stabilizers | 1.0 |
| Water | to 100 |
| Phosphoric acid | to pH 4.0 |

| Part III | % by Weight |
|---|---|
| Propellant 12 | 50.0 |
| Propellant 114 | 50.0 |

The parts were packaged in a container of the type shown in U.S. Pat. No. 3,241,722. In the inner container was placed 27.0 parts by weight of Part II. In the outer container was placed 93.0 parts of Part I together with 9.3 parts of Part III. The wall separating the inner from the outer container was formed of synthetic plastic material (polyethylene) permeable to peroxide and more readily ruptured by pressure than the outer metallic wall of the container. The free space left was approximately 40%. When the contents of the two containers were dispensed simultaneously at room temperature onto tresses of light brown untreated human hair, there was produced a light-colored foam of fine texture which was worked into the fibers with the fingers. After 20 minutes, the tresses were rinsed and shampooed, exhibiting an attractive light blonde shade.

Of the total content of dye intermediate and modifier included in the composition of this example, only a small proportion is needed for color development. The addition of the beta-naphthol serves to minimize the development of oxygen pressure in the event of inadvertent mixing inside the container, contributing little to the final shade of color produced. The pressure within the container, without mixing of the parts, was 45 p.s.i.g.; 3 days after intentional mixing of all of Parts I-III within the container by rupture of the separating wall the pressure was only 52 p.s.i.g. Example IV The following compositions were prepared:

| Part I | % by Weight |
|---|---|
| Oleic acid | 8.7 |
| Octyl phenoxy polyethoxy ethanol | 6.0 |
| Isopropanol | 10.0 |
| Monoethanolamine | 3.2 |
| p-Phenylenediamine | 0.63 |
| Resorcinol | 0.16 |
| p-Aminophenol | 0.05 |
| 4,4-Diaminodiphenylamine sulfate | 0.2 |
| Water | to 100 |

| Part II | % by Weight |
|---|---|
| Hydrogen peroxide | 9.0 |
| Stabilizers | 1.0 |
| Water | to 100 |
| Phosphoric acid | to pH 4.0 |

| Part III | % by Weight |
|---|---|
| Propellant 12 | 50.0 |
| Propellant 114 | 50.0 |

The parts, packaged and evaluated as described in Example III, produced an attractive dark brown color on previously untreated human hair.

The composition of this example represents a pressure packaged hair dyeing system in which all of the intermediates and modifiers present contribute to the final shade produced. The pressure within the container before mixing of the parts was 45 p.s.i.g.; after mixing all of the parts within the container and allowing to stand 3 days the pressure was unchanged.

Example V

In order to simulate the results achieved when the peroxide solution undergoes spontaneous decomposition with the liberation of gaseous oxygen, there was introduced into a conventional aerosol single compartment container 90 parts by weight of a conventional dye base component together with beta-naphthol, as follows:

| | % by Weight |
|---|---|
| Oleic acid | 8.7 |
| Monoethanolamine | 6.7 |
| Isopropanol | 1.9 |
| Octyl phenoxy polyethoxy ethanol | 1.9 |
| Lauryl alcohol | 0.4 |
| Beta-napthol | 1.8 |
| Water | to 100 |

The container was then pressurized to 54 p.s.i.g. with oxygen; the pressure was measured at intervals thereafter and was found to decrease to 51 p.s.i.g. after 5 hours and to continue to decrease thereafter, reaching zero (atmospheric) after 7 days. When the test was repeated but omitting the beta-naphthol, the pressure remained unchanged at 54 p.s.i.g. for more than 7 days.

What is claimed is:

1. A dispensing container having two compartments providing separate storage of two parts of a hair treating composition selected from the group consisting of aqueous hydrogen peroxide hair bleach and aqueous oxidative hair dye compositions and means including a pressure propellant for dispensing the contents of both compartments simultaneously with mixing thereof, the contents of one compartment comprising an aqueous medium containing an alkalizing agent sufficient to provide a pH from 7.0 to 12 in the mixed composition and a control compound which is a member of the group consisting of o-aminophenol, p-aminophenol, methyl-p-aminophenol, 4-amino-3-methylphenol, 2,4-diaminophenol, N-(p-hydroxyphenyl) glycine, p-phenylenediamine, p-tolylenediamine, 1,2,4,5-tetrahydroxybenzene, betanaphthol, 2,5-dihydroxybenzoic acid, 3,4 -dihydroxybenzoic acid, gallic acid, propyl gallate, 2,7-naphthalenediol, 2,2',4,4'-tetrahydroxybiphenyl, hydroquinone monosulfonic acid, 3,4,5-trihydroxyacetophenone, 3-(N,N,-dimethylamino) phenol, 8-hydroxyquinoline, pyrocatechol, resorcinol, hydroquinone, pyrogallol, 1,3,5-trihydroxybenzene, 4-t-butyl catechol, 1,5-naphthalenediol, 3-hydroxydiphenylamine, m-phenylene diamine, 2,4-diaminoanisol, and mixtures thereof, and the contents of the other compartment comprising an aqueous hydrogen peroxide solution, the amount of hydrogen peroxide being from 0.1 to 6% by weight of the total contents of the container excluding pressure propellant, the amount of total control compound being from 10 to 500% by weight of the hydrogen peroxide and sufficient to prevent liberation of oxygen gas in an amount to produce total pressure in the package greater than 150 p.s.i.g. if mixing of the two parts within the package occurs.

2. A container as claimed in claim 1 in which said hair treating composition is an oxidative dye composition and the two compartments are separated by a wall of synthetic plastic material permeable to a portion of the contents of at least one compartment.

3. A container as claimed in claim 1 in which said control compound is a mixture including a first compound selected from the group consisting of o-aminophenol, p-aminophenol, methyl-p-aminophenol, 4-amino-3-methylphenol, 2,4-diaminophenol, N-(p-hydroxyphenyl) glycine, p-phenylenediamine, p-tolylenediamine, 1,2,4,5-tetrahydroxybenzene and mixtures thereof, and a second compound selected from the group consisting of beta-naphthol, 2,5-dihydroxybenzoic acid, 3,4 -dihydroxybenzoic acid, gallic acid, propyl gallate, 2,7-naphthalenediol, 2,2',4,4'-tetrahydroxybiphenyl, hydroquinone monosulfonic acid, 3,4,5-trihydroxyacetophenone, 3-(N,N-dimethylamino) phenol, 8-hydroxy-quinoline, pyrocatechol, resorcinol, hydroquinone, pyrogallol, 1,3,5-trihydroxybenzene, 4-t-butyl catechol, 1,5-naphthalenediol, 3-hydroxydiphenylamine, m-phenylenediamine, 2,4-diaminoanisole, and mixtures thereof, the amount of said first compound being less than the amount of said second compound.

4. A container as claimed in claim 1 in which the control compound is beta-naphthol.

5. A container as claimed in claim 1 in which the control compound is 2,5 -dihydroxybenzoic acid.

6. A container as claimed in claim 1 in which the two compartments are separated by a wall of synthetic plastic material permeable to a portion of the contents of at least one compartment.

7. A container as claimed in claim 1 in which said hair treating composition is aqueous hydrogen peroxide hair bleach.

8. A container as claimed in claim 1 in which the total free space within the container, including both compartments, is from 10 to 40%.

9. A container as claimed in claim 3 in which the total free space within the container, including both compartments, is from 10 to 40%.

10. A container as claimed in claim 3 in which said hair treating composition is an oxidative dye composition and the two compartments are separated by a wall of synthetic plastic material permeable to a portion of the contents of at least one compartment.

11. A container as claimed in claim 4 in which said hair treating composition is an oxidative dye composition and the two compartments are separated by a wall of synthetic plastic material permeable to a portion of the contents of at least one compartment.

12. A container as claimed in claim 5 in which said hair treating composition is an oxidative dye composition and the two compartments are separated by a wall of synthetic plastic material permeable to a portion of the contents of at least one compartment.

13. A container as claimed in claim 1 in which the total free space within the container, including both compartments, is from 10 to 25%, and the total amount of said control compound is at least 25% by weight of the peroxide.

14. A container as claimed in claim 13 in which said hair treating composition is an oxidative dye composition and the two compartments are separated by a wall of synthetic plastic material permeable to a portion of the contents of at least one compartment.

15. A container as claimed in claim 10 in which the total free space within the container, including both compartments, is from 10 to 40%.

16. A container as claimed in claim 11 in which the total free space within the container, including both compartments, is from 10 to 40%.

17. A container as claimed in claim 12 in which the total free space within the container, including both compartments, is from 10 to 40%.

* * * * *